United States Patent [19]
Langevine et al.

[11] Patent Number: 5,635,449
[45] Date of Patent: Jun. 3, 1997

[54] ARYLTHIOALKYL- AND ARYLTHIOALKENYLPHOSPHONIC ACIDS AND DERIVATIVES THEREOF USEFUL AS HERBICIDAL AGENTS

[75] Inventors: Charles M. Langevine, Brooklyn, N.Y.; John M. Finn, Mercerville, N.J.

[73] Assignee: American Cyanamid Company, Madison, N.J.

[21] Appl. No.: 418,985

[22] Filed: Apr. 7, 1995

[51] Int. Cl.$^6$ .............................. A01N 57/30; C07F 9/40; C07F 9/38
[52] U.S. Cl. ............... 504/207; 558/180; 558/184; 558/187; 562/11; 562/23; 562/24
[58] Field of Search ............... 504/207; 558/184, 558/187, 180; 562/11, 23, 24

[56] References Cited

U.S. PATENT DOCUMENTS

| | | | |
|---|---|---|---|
| 2,963,505 | 12/1960 | Muhlmann et al. | 558/184 |
| 2,999,874 | 9/1961 | Schrader | 558/184 |
| 4,456,464 | 6/1984 | Lee et al. | 558/184 X |

OTHER PUBLICATIONS

CA 114: 201751s (1991).
C. U. Kim, et at, Journal of Medicinal Chemistry, 33, pp. 1207–1213 (1990).
S. J. Hays, et al, Journal of Medicinal Chemistry, 33, pp. 2916–2924 (1990).
C. E. Nakamura, et al, Biochemical Pharmacology, 35, pp. 133–136 (1986).

*Primary Examiner*—Robert W. Ramsuer
*Assistant Examiner*—Michael G. Ambrose
*Attorney, Agent, or Firm*—Charles F. Costello, Jr.

[57] ABSTRACT

The present invention provides arylthioalkyl- and arylthioalkenylphosphonic acids and derivatives thereof having the structural formula I

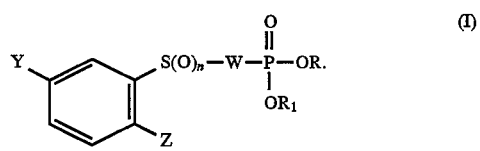

Further provided are compositions and methods comprising those compounds for the control of undesirable plant species.

24 Claims, No Drawings

ARYLTHIOALKYL- AND ARYLTHIOALKENYLPHOSPHONIC ACIDS AND DERIVATIVES THEREOF USEFUL AS HERBICIDAL AGENTS

BACKGROUND OF THE INVENTION

Weeds cause tremendous global economic losses by reducing crop yields and lowering crop quality. In the United States, crops must compete with hundreds of different weed species such as lambsquarters and wild mustard.

Lambsquarters and wild mustard are particularly troublesome weed species because it is difficult to control them with certain of the commercial herbicides available today. Accordingly, there is ongoing research to create new herbicidal agents for their control.

It is an object of the present invention to provide compounds which are effective for controlling undesirable plant species.

It is a feature of this invention to provide compounds which are effective for the control of lambsquarters and wild mustard.

It is also an object of the present invention to provide a method for controlling undesirable plant species.

These and other objects of the present invention will become more apparent from the detailed description thereof set forth below.

SUMMARY OF THE INVENTION

The present invention describes arylthioalkyl- and arylthioalkenylphosphonic acids and derivatives thereof which are useful as herbicidal agents.

The arylthioalkyl- and arylthioalkenylphosphonic acids and derivatives of the present invention have the structural formula I

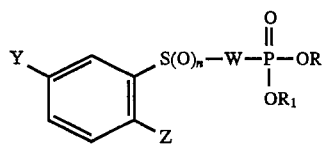

wherein

Y is hydrogen or halogen;

Z is $NH_2$ or $OR_2$;

$R_2$ is hydrogen, $C_1$–$C_4$alkylcarbonyl or benzoyl;

n is an integer of 0, 1 or 2;

W is —$(CH_2)_4$—, —$CH_2CH=CHCH_2$— or —$CH_2CH_2CH=CH$—; and

R and $R_1$ are each independently hydrogen, $C_1$–$C_4$alkyl, $C_1$–$C_4$alkylcarbonyloxymethylene or an alkali metal, ammonium or organic ammonium cation.

This invention also relates to compositions containing those compounds and methods for using those compounds and compositions. It has been found that the arylthioalkyl- and arylthioalkenylphosphonic acids and derivatives of this invention, and compositions containing them, are useful for the postemergence control of undesirable plant species.

DETAILED DESCRIPTION OF THE INVENTION

The present invention provides a method for controlling undesirable plant species which comprises applying to the foliage and stems of said plants a herbicidally effective amount of a formula I, arylthioalkyl- or arylthioalkenylphosphonic acid or a derivative thereof.

The arylthioalkyl- and arylthioalkenylphosphonic acids and derivatives of the present invention have the structural formula I

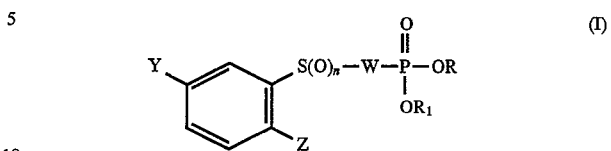

wherein

Y is hydrogen or halogen;

Z is $NH_2$ or $OR_2$;

$R_2$ is hydrogen, $C_1$–$C_4$alkylcarbonyl or benzoyl;

n is an integer of 0, 1 or 2;

W is —$(CH_2)_4$—, —$CH_2CH=CHCH_2$— or —$CH_2CH_2CH=CH$—; and

R and $R_1$ are each independently hydrogen, $C_1$–$C_4$alkyl, $C_1$–$C_4$alkylcarbonyloxymethylene or an alkali metal, ammonium or organic ammonium cation.

Preferred formula I herbicidal agents of the present invention are those wherein Y is hydrogen, F or Br;

Z is $NH_2$ or $OR_2$;

$R_2$ is hydrogen, $C_1$–$C_4$alkylcarbonyl or benzoyl;

n is an integer of 0 or 1;

W is —$(CH_2)_4$— or —$CH_2CH_2CH=CH$—; and

R and $R_1$ are each independently hydrogen, $C_1$–$C_4$alkyl, $C_1$–$C_4$alkylcarbonyloxymethylene or an alkali metal or organic ammonium cation.

Arylthioalkyl- and arylthioalkenylphosphonic acids and derivatives of the present invention which are particularly effective herbicidal agents include {4-[(o-hydroxyphenyl)thio]-1-butenyl}phosphonic acid;

diethyl {4-[(o-aminophenyl)thio]butyl}phosphonate;

dilithium {4-[(o-aminophenyl)thio]butyl}phosphonate;

{4-[(o-aminophenyl)thio]butyl}phosphonic acid, compound with cyclohexylamine (1:2);

dipivalate ester of bis(hydroxylmethyl) {4-[(o-hydroxyphenyl) thio]butyl}phosphonate;

{4-[(o-hydroxyphenyl)sulfinyl]butyl}phosphonic acid, compound with cyclohexylamine (1:2);

{4-[(o-hydroxyphenyl)thio]butyl}phosphonic acid, compound with N,N,N',N'-tetramethylethylenediamine;

{4-[(o-hydroxyphenyl)sulfinyl]butyl}phosphonic acid;

{4-[(o-hydroxyphenyl)thio]butyl}phosphonic acid, arylbutyrate ester; and

{4-[(o-hydroxyphenyl)thio]-1-butenyl}phosphonic acid, compound with isopropylamine (1:2), among others.

Exemplary of halogen hereinabove are fluorine, chlorine, bromine and iodine. In formula I above, alkali metals include: sodium, potassium and lithium. Further, the term organic ammonium is defined as a group consisting of one or two positively charged nitrogen atoms each joined to from one to four $C_1$–$C_{16}$alkyl groups, provided that when the group contains two positively charged nitrogen atoms, the organic ammonium cations R and $R_1$ are each present in the same group.

Advantageously, it has been found that the compounds of this invention are particularly useful for the post-emergence control of lambsquarters and wild mustard.

Formula I compounds wherein Z is NH₂ or OH, n is 0, W is —(CH₂)₄— or —CH₂CH=CHCH₂— and R and R₁ are C₁–C₄-alkyl may be prepared by reacting a dialkyl bromophosphonate of formula II with a substituted thiophenol of formula III in the presence of an organic base such as triethylamine. The reaction scheme is shown in Flow Diagram I.

FLOW DIAGRAM I

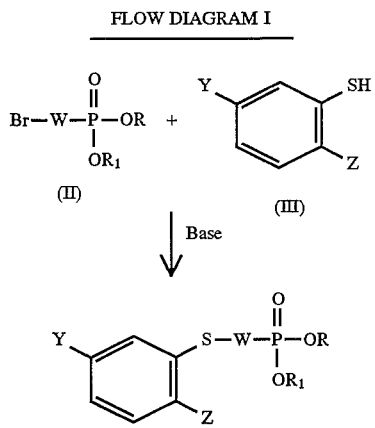

Arylthioalkenylphosphonate compounds of formula I wherein Z is NH₂ or OH, n is 0, W is —CH₂CH₂CH=CH— and R and R₁ are C₁–C₄alkyl may be prepared by reacting a substituted thiophenol of formula III with 2-bromoethyldioxolane to form a 2-[(substituted phenyl)thio]ethyldioxolane of formula IV, deprotecting the dioxolane group of the formula IV compound using standard conditions such as aqueous acid to form a 3-[(o-substituted phenyl)thio]propionaldehyde of formula V, and reacting the formula V compound with a tetra(C₁–C₄alkyl) methylenediphosphonate of formula VI in the presence of n-butyllithium. The reaction scheme is shown below in Flow Diagram II.

FLOW DIAGRAM II

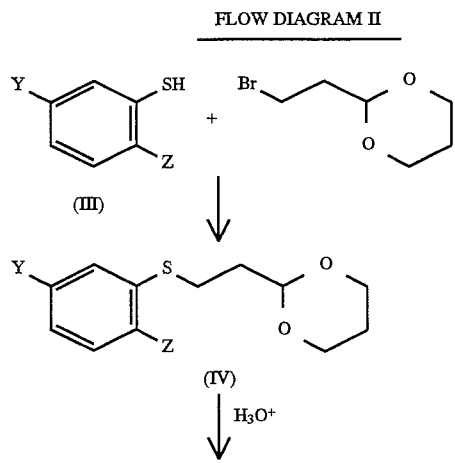

-continued
FLOW DIAGRAM II

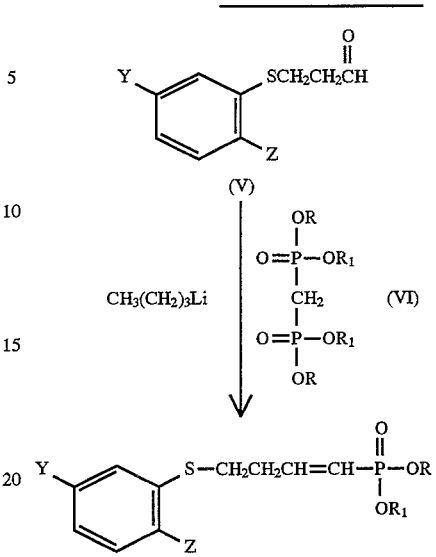

Arylthioalkyl- and arylthioalkenylphosphonic acid compounds of formula I wherein R and R₁ are hydrogen and n is 0 may be prepared by reacting a formula I compound wherein R and R₁ are C₁–C₄alkyl and n is 0 with bromotrimethylsilane in the presence of an inert solvent such as methylene chloride to form and intermediate compound and hydrolyzing the intermediate compound with methanol. The reaction scheme is shown in Flow Diagram III.

FLOW DIAGRAM III

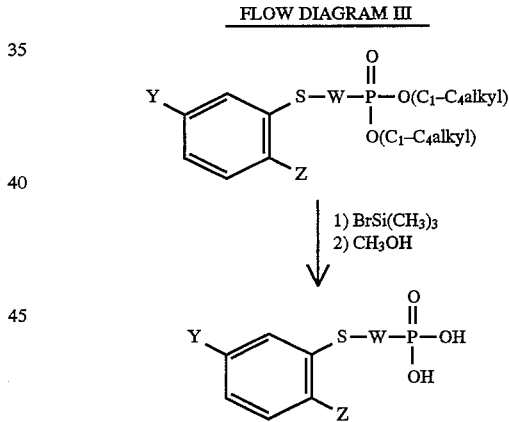

Compounds of formula I wherein n is 1 or 2 may be prepared by oxidizing a formula I compound wherein n is 0 using standard conditions such as treatment with 3-chloroperoxybenzoic acid. The reaction scheme is shown below in Flow Diagram IV.

FLOW DIAGRAM IV

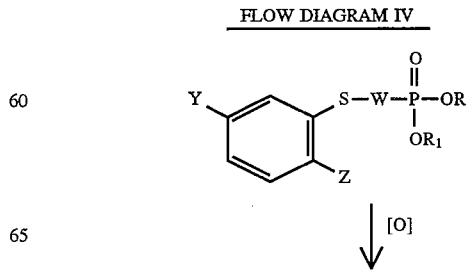

-continued
FLOW DIAGRAM IV

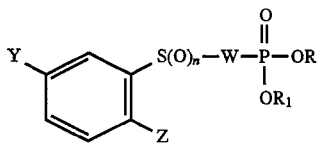

Certain formula I compounds wherein Y is Cl, Br or I and W is —(CH$_2$)$_4$— may be prepared by halogenating a formula I compound wherein Y is hydrogen and W is —(CH$_2$)$_4$— with a halogenating agent such as bromine, chlorine, N-bromosuccinimide, N-chlorosuccinimide, N-iodosuccinimide and the like in the presence of an inert solvent. The reaction is shown in Flow Diagram V.

FLOW DIAGRAM V

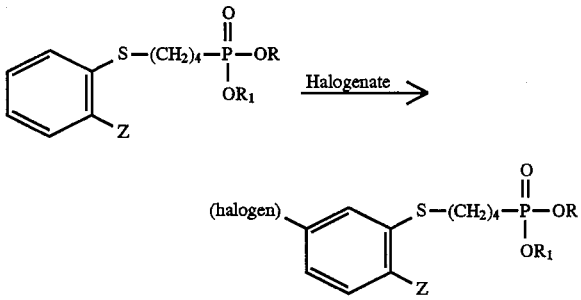

Arylthioalkyl- and arylthioalkenylphosphonate compounds of formula I wherein R$_2$ is C$_1$–C$_4$alkylcarbonyl or benzoyl may be prepared by reacting a formula I compound wherein R$_2$ is hydrogen and R and R$_1$ are C$_1$–C$_4$alkyl with an acid chloride of formula VII in the presence of a base such as triethylamine. The reaction scheme is shown below in Flow Diagram VI.

FLOW DIAGRAM VI

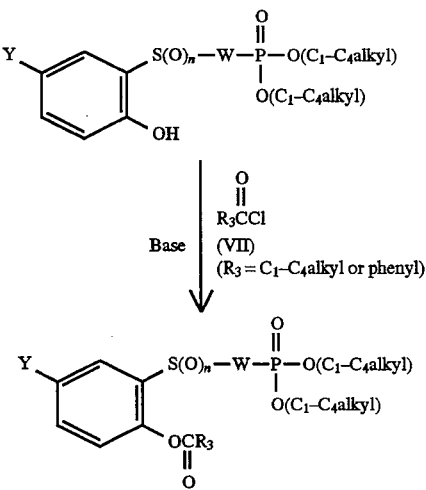

Compounds of formula I wherein R and R$_1$ are C$_1$–C$_4$alkylcarbonyloxymethylene may be prepared by reacting a formula I compound wherein R and R$_1$ are hydrogen with a C$_1$–C$_4$alkylcarbonyloxymethylene chloride compound of formula VIII in the presence of a base such as triethylamine. The reaction is shown in Flow Diagram VII.

FLOW DIAGRAM VII

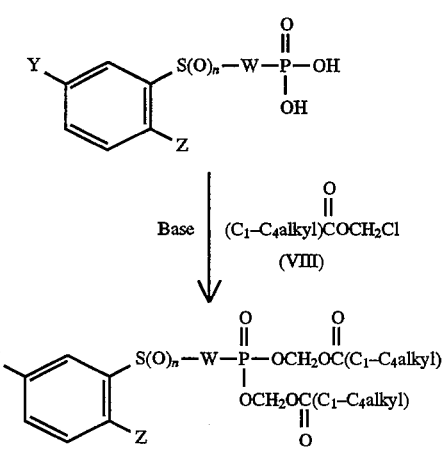

Advantageously, formula I compounds wherein R and/or R$_1$ are an alkali metal, ammonium or organic ammonium cation may be prepared from formula I compounds wherein R and/or R$_1$ are hydrogen by conventional methods known to those skilled in the art.

The arylthioalkyl- and arylthioalkenylphosphonic acids and derivatives of the present invention are effective herbicidal agents useful for the postemergence control of a variety of undesirable plant species. Those compounds are especially useful for the postemergence control of lambsquarters and wild mustard. The compounds are effective for controlling weeds native to both dry land and wet land areas and are effective in controlling the above-said plants when applied to the foliage and stems thereof at rates of from about 0.5 kg/ha to 10 kg/ha.

The compounds of this invention are best suited for use as broad spectrum herbicides. However, certain compounds of this invention are selective. In fact, some of the compounds of this invention are selective in crops such as corn and rice. Further, certain compounds of this invention are useful for regulating the plant growth of a wide variety of plant species.

The compounds of this invention may be used in combination with other biological chemicals, including other herbicides.

The arylthioalkyl- and arylthioalkenylphosphonic acids and derivatives of this invention may be applied to undesirable plant species in the form of a solid or liquid herbicidal composition comprising a herbicidally effective amount of the compound dispersed or dissolved in an agronomically acceptable, inert solid or liquid carrier.

The compounds of the present invention may be formulated as emulsifiable concentrates, wettable powders, granular formulations, flowable concentrates and the like.

In order to facilitate a further understanding of the invention, the following examples are presented primarily for the purpose of illustrating more specific details thereof. The invention should not be deemed limited by the examples as the full scope of the invention is defined in the claims. The term NMR designates nuclear magnetic resonance spectroscopy.

EXAMPLE 1

Preparation of Diethyl {4-[(o-aminophenyl)thio]butyl}phosphonate

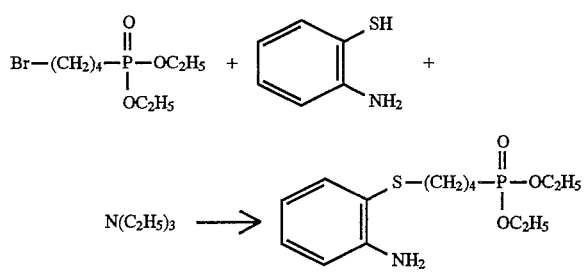

Triethylamine (0.1 mol) is slowly added to a mixture of diethyl (4-bromobutyl)phosphonate (0.1 mol) and o-aminothiophenol (0.1 mol) in tetrahydrofuran at 0° C. The reaction mixture is stirred at 0° C. for 4 hours, at room temperature for 16 hours and poured into water. The aqueous mixture is extracted with ether. The organic extracts are combined, dried over anhydrous magnesium sulfate and concentrated in vacuo to obtain a residue. Column chromatography of the residue using silica gel, a 1:1 ethyl acetate/hexane solution and a 1:9 methanol/ethyl acetate solution gives the title product as a clear yellow liquid which is identified by NMR spectral analyses.

Using essentially the same procedure, but using the appropriately substituted phenol or thiophenol and the appropriately substituted phosphonate, the following compounds are obtained:

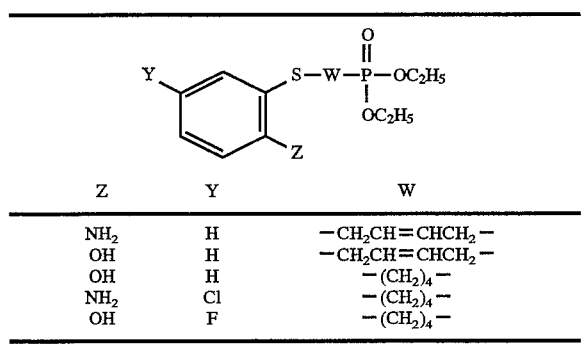

| Z | Y | W |
|---|---|---|
| $NH_2$ | H | $-CH_2CH=CHCH_2-$ |
| OH | H | $-CH_2CH=CHCH_2-$ |
| OH | H | $-(CH_2)_4-$ |
| $NH_2$ | Cl | $-(CH_2)_4-$ |
| OH | F | $-(CH_2)_4-$ |

EXAMPLE 2

Preparation of {4-[(o-Aminophenyl)thio]butyl}phosphonic acid

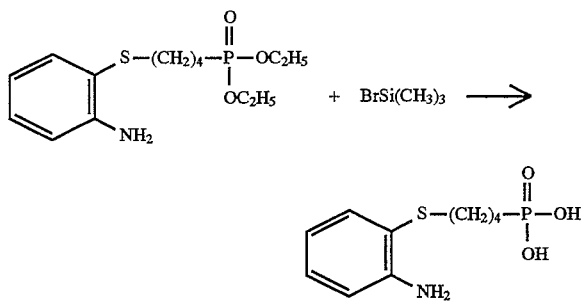

A mixture of diethyl {4-[(o-aminophenyl)thio]butyl}phosphonate (0.1 mol) and bromotrimethylsilane (0.3 mol) in methylene chloride is stirred at room temperature for 16 hours, concentrated in vacuo, diluted with methanol, stirred at room temperature for 2 hours and concentrated in vacuo to give the title product as a clear viscous liquid which is identified by NMR spectral analyses.

Using essentially the same procedure, the following compounds are obtained:

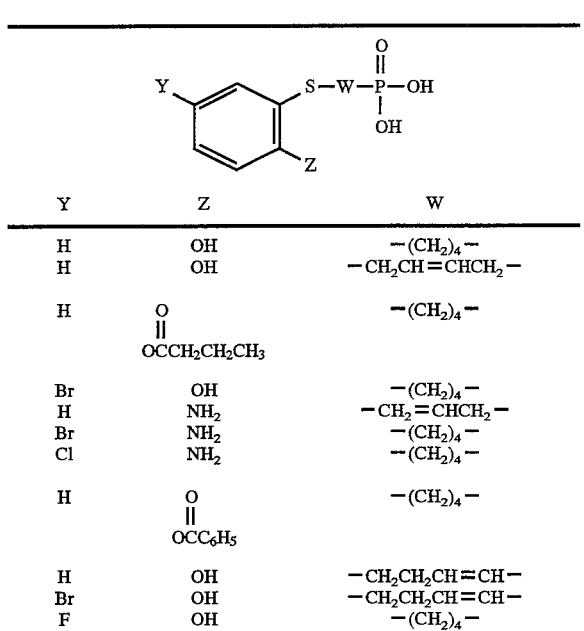

| Y | Z | W |
|---|---|---|
| H | OH | $-(CH_2)_4-$ |
| H | OH | $-CH_2CH=CHCH_2-$ |
| H | $\underset{OCCH_2CH_2CH_3}{\overset{O}{\|}}$ | $-(CH_2)_4-$ |
| Br | OH | $-(CH_2)_4-$ |
| H | $NH_2$ | $-CH_2=CHCH_2-$ |
| Br | $NH_2$ | $-(CH_2)_4-$ |
| Cl | $NH_2$ | $-(CH_2)_4-$ |
| H | $\underset{OCC_6H_5}{\overset{O}{\|}}$ | $-(CH_2)_4-$ |
| H | OH | $-CH_2CH_2CH=CH-$ |
| Br | OH | $-CH_2CH_2CH=CH-$ |
| F | OH | $-(CH_2)_4-$ |

EXAMPLE 3

Preparation of {4-[(o-Aminophenyl)thio]butyl}phosphonic acid, monoethyl ester

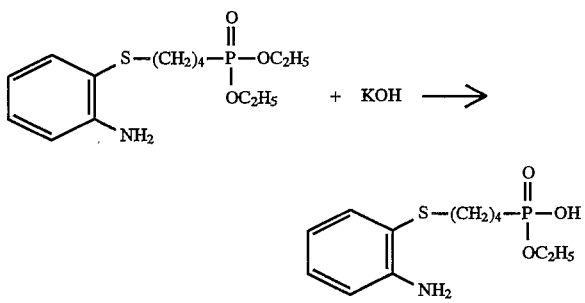

A mixture of diethyl {4-[(o-aminophenyl)thio]butyl}phosphonate (0.1 mol) and potassium hydroxide (0.2 mol) in ethanol is refluxed for 16 hours, cooled to room temperature, concentrated in vacuo, diluted with water, acidified with 10% hydrochloric acid and extracted with ether. The organic extracts are combined, dried over anhydrous magnesium sulfate and concentrated in vacuo to give the title product as a viscous tan liquid which is identified by NMR spectral analyses.

Using essentially the same procedure, but substituting diethyl {4-[(o-hydroxyphenyl)thio]butyl}phosphonate for diethyl {4-[(o-aminophenyl)thio]butyl}phosphonate, {4-[(o-hydroxyphenyl)thio]butyl}phosphonic acid, monoethyl ester is obtained as a tan liquid.

EXAMPLE 4

Preparation of {4-[(o-Aminophenyl)thio]butyl}phosphonic acid, compound with cyclohexylamine (1:2)

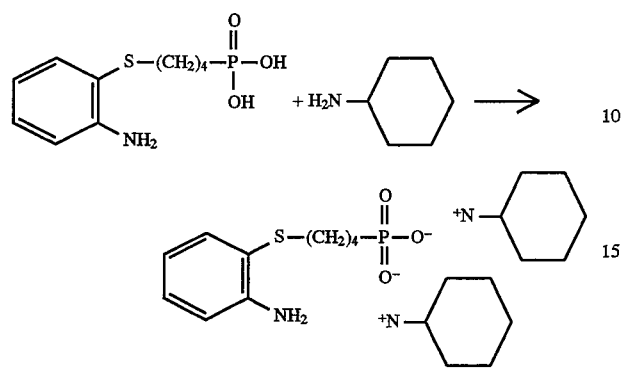

A mixture of {4-[(o-aminophenyl)thio]butyl}phosphonic acid (0.1 mol) and cyclohexylamine (0.3 mol) is refluxed for 2 hours and concentrated in vacuo to obtain a residue. The residue is washed with ether and dried to give the title product as a tan solid which is identified by NMR spectral analysis.

Using essentially the same procedure, the following compounds are obtained:

EXAMPLE 5

Preparation of {4-[(o-Aminophenyl)thio]butyl}phosphonic acid, dilithium salt

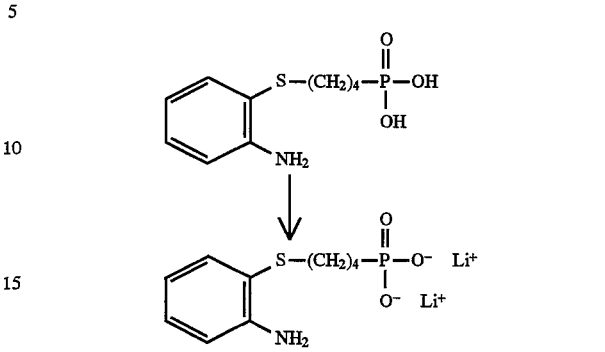

An ion-exchange column is filled with an ion-exchange resin (25 g, 50×8 Dowex), washed with water and treated with 2N lithium hydroxide solution (500 mL). A solution of {4-[(o-aminophenyl)thio]butyl}phosphonic acid (1.04 g, 4 mmol) in water is added to the column and the column is eluted with water. Fractions containing the desired product are combined and concentrated in vacuo to give the title product as a white solid which is identified by NMR spectral analyses.

| Y | Z | W | n | R | $R_1$ |
|---|---|---|---|---|---|
| H | $NH_2$ | $-(CH_2)_4-$ | 0 | $CH_3$<br>\|<br>$^+N-CH_2-CH_2-N^+$<br>\|<br>$CH_3$ | $CH_3$<br>\|<br>$CH_3$ |
| H | OH | $-(CH_2)_4-$ | 1 | $^+N-\bigcirc$ | $^+N-\bigcirc$ |
| H | OH | $-(CH_2)_4-$ | 0 | $^+N-\bigcirc$ | $^+N-\bigcirc$ |
| H | OH | $-(CH_2)_4-$ | 0 | $CH_3$<br>\|<br>$^+N-CH_2-CH_2-N^+$<br>\|<br>$CH_3$ | $CH_3$<br>\|<br>$CH_3$ |
| H | OH | $-(CH_2)_4-$ | 0 | $^+N[CH(CH_3)_2]_2$ | $^+N[CH(CH_3)_2]_2$ |
| F | OH | $-(CH_2)_4-$ | 0 | $^+N[CH(CH_3)_2]_2$ | $^+N[CH(CH_3)_2]_2$ |
| H | OH | $CH_2CH_2CH=CH$ | 0 | $^+N[CH(CH_3)_2]_2$ | $^+N[CH(CH_3)_2]_2$ |

EXAMPLE 6

Preparation of Diethyl {4-[(2-amino-5-bromophenyl)thio]butyl}phosphonate

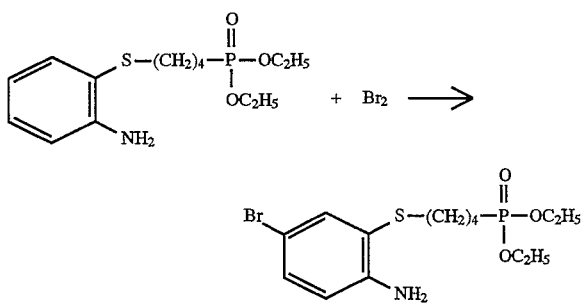

Bromine (0.75 g, 4.7 mmol) is added to a solution of diethyl {4-[(o-aminophenyl)thio]butyl}phosphonate (1.36 g, 4.3 mmol) in methylene chloride at 0° C. The reaction mixture is stirred for 35 minutes at 0° C. and diluted with a 5% sodium sulfite solution. The layers are separated and the aqueous layer is washed with methylene chloride. The organic layer and the methylene chloride washes are combined, dried over anhydrous magnesium sulfate and concentrated in vacuo to obtain a residue. Chromatography of the residue using silica gel and 0–4% methanol in hexanes:ethyl acetate (1:1) solutions gives the title product as a yellow liquid which is identified by NMR spectral analyses.

Using essentially the same procedure, but substituting diethyl {4-[(o-hydroxyphenyl)thio]butyl}phosphonate for diethyl {4-[(o-aminophenyl)thio]butyl}phosphonate, diethyl {4-[(5-bromo-2-hydroxyphenyl)thio]butyl}phosphonate is obtained as a tan liquid.

EXAMPLE 7

Preparation of {4-[(2-Hydroxyphenyl)thio]butyl}phosphonic acid, diethyl ester, aryl-benzoate (ester)

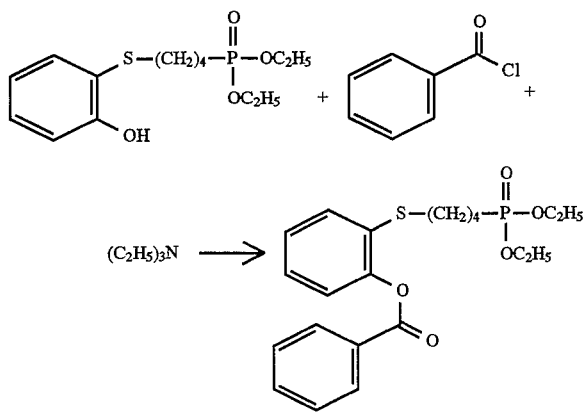

Benzoyl chloride (14.06 g, 0.1 mol) is slowly added to a mixture of diethyl {4-[(o-hydroxyphenyl)thio]butyl}phosphonate (31.8 g, 0.1 mol) and triethylamine (20.2 g, 0.2 mol) in diethyl ether at 0° C. The reaction mixture is stirred at room temperature for about 16 hours, washed sequentially with 10% hydrochloric acid, water, 10% sodium bicarbonate solution and water, dried over anhydrous magnesium sulfate and concentrated in vacuo to give the title product as a tan liquid which is identified by NMR spectral analyses.

Using essentially the same procedure, but substituting butyryl chloride for benzoyl chloride, {4-[(o-hydroxyphenyl)thio]butyl}phosphonic acid, diethyl ester, aryl-butyrate (ester) is obtained as a tan liquid.

EXAMPLE 8

Preparation of Diethyl {4-[(o-aminophenyl)sulfonyl]butyl}phosphonate

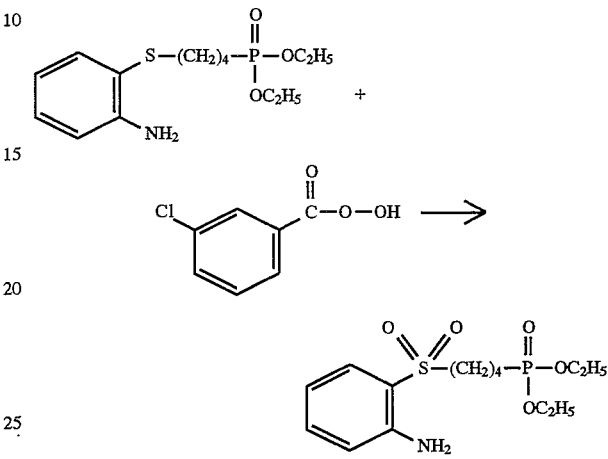

A solution of 3-chloroperoxybenzoic acid (0.95 g, 0.005 mol) in methylene chloride is added to a solution of diethyl {4-[(o-aminophenyl)thio]butyl}phosphonate (1.75 g, 0.005 mol) in methylene chloride at 0° C. The reaction mixture is stirred at room temperature for 3 hours and filtered. The filtrate is concentrated in vacuo to give a solid. The solid is mixed with petroleum ether and the mixture is decanted and concentrated in vacuo to give the title product as a tan liquid which is identified by NMR spectral analyses.

Using essentially the same procedure, but substituting {4-[(o-hydroxyphenyl)thio]butyl}phosphonic acid for diethyl {4-[(o-aminophenyl)thio]butyl}phosphonate and using one or two molar equivalents of 3-chloroperoxybenzoic acid, {4-[(o-hydroxyphenyl)sulfinyl]butyl}phosphonic acid and {4-[(o-hydroxyphenyl)sulfonyl]butyl}phosphonic acid are obtained, respectively.

EXAMPLE 9

Preparation of {4-[(o-Hydroxyphenyl)thio]butyl}phosphonic acid, bis(hydroxymethyl)ester, dipivalate ester

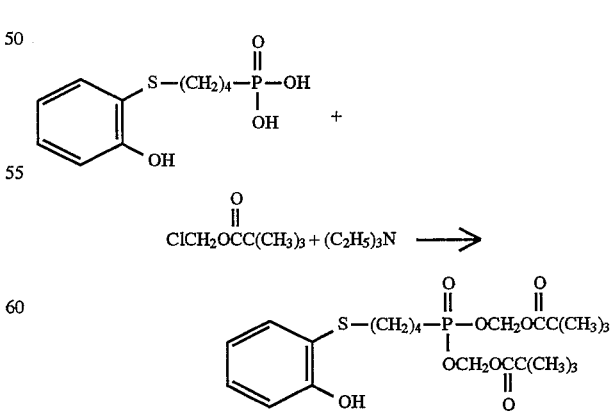

A mixture of {4-[(o-hydroxyphenyl)thio]butyl}phosphonic acid (1.8 g, 0.007 mol) and triethylamine (5 mL) is refluxed for 4 hours, treated with chloromethyl pivalate (1.8 g, 0.012 mol), refluxed for 3 days and diluted with water. The aqueous mixture is extracted with methylene chloride. The organic extracts are combined and concentrated in vacuo to obtain a residue. Chromatography of the residue using silica gel and a 2:3 ethyl acetate/hexanes solution gives the title product as a pale yellow liquid which is identified by NMR spectral analyses.

EXAMPLE 10

Preparation of Diethyl {4-[(o-hydroxyphenyl)thio]-1-butenyl}phosphonate

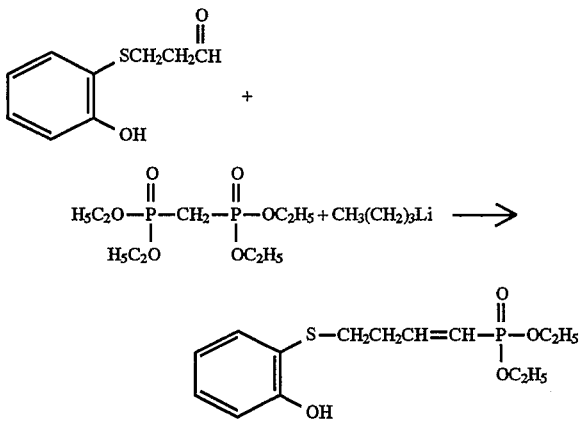

A solution of n-butyllithium (0.11 mol) in tetrahydrofuran is cooled to −78° C., treated with tetraethyl methylenediphosphonate (0.1 mol), stirred at −78° C. for 30 minutes, treated with a solution of 3-[(o-hydroxyphenyl)thio] propionaldehyde (0.1 mol) in tetrahydrofuran, stirred for one hour at −78° C. and for one hour at room temperature, and diluted with brine (40 mL) and 2N hydrochloric acid (3 mL). The aqueous mixture is extracted with diethyl ether. The organic extracts are combined, washed sequentially with 10% hydrochloric acid and water, dried over anhydrous magnesium sulfate and concentrated in vacuo to obtain a residue. High performance liquid chromatography of the residue using silica gel and 0–6% methanol in hexanes:ethyl acetate (1:1) solutions gives the title product as a yellow oil which is identified by NMR spectral analyses.

Using essentially the same procedure, but substituting 3-[(5-bromo-2-hydroxyphenyl)thio]propionaldehyde for 3-[(o-hydroxyphenyl)thio]propionaldehyde, diethyl {4-[(5-bromo-2-hydroxyphenyl)thio]-1-butenyl}phosphonate is obtained as a yellow oil.

EXAMPLE 11

Herbicidal evaluation of test compounds

The herbicidal activity of the compounds of the present invention is demonstrated by the following tests, wherein a variety of dicotyledonous and monocotyledonous plants are treated with test compounds, dispersed in aqueous acetone mixtures. In the tests, seedling plants are grown in jiffy flats for about two weeks. The test compounds are dispersed in 50/50 acetone/water mixtures containing 0.5% TWEEN®20, a polyoxyethylene sorbitan monolaurate surfactant of Atlas Chemical Industries, in sufficient quantities to provide the equivalent of about 1.0 kg to 8.0 kg per hectare of test compound when applied to the plants through a spray nozzle operating at 40 psi for a predetermined time. After spraying, the plants are placed on greenhouse benches and are cared for in the usual manner, commensurate with conventional greenhouse practices. From four to five weeks after treatment, the seedling plants are examined and rated according to the rating system set forth below. Data obtained are reported in Table I below. Where more than one test is involved for a given compound, the data are averaged.

Plant species employed are reported by header abbreviation, common name and scientific name.

Compounds employed in this herbicidal evaluation are given a compound number and identified by name. Data in Table I are reported by compound number.

Herbicide Rating Scale

Results of herbicide evaluation are expressed on a rating scale (0–9). The scale is based upon a visual observation of plant stand, vigor, malformation, size, chlorosis and overall plant appearance as compared with a control.

| Rating | Meaning | % Control Compared to Check |
|---|---|---|
| 9 | Complete Kill | 100 |
| 8 | Approaching Complete Kill | 91–99 |
| 7 | Good Herbicidal Effect | 80–90 |
| 6 | Herbicidal Effect | 65–79 |
| 5 | Definite Injury | 45–64 |
| 4 | Injury | 30–44 |
| 3 | Moderate Effect | 16–29 |
| 2 | Slight Effect | 6–15 |
| 1 | Trace Effect | 1–5 |
| 0 | No Effect | 0 |
| — | No Evaluation | |

| PLANT SPECIES EMPLOYED IN HERBICIDAL EVALUATIONS | | |
|---|---|---|
| Header Abb. | Common Name | Scientific Name |
| AMASS | PIGWEED SPP. | AMARANTHUS SPP. |
| CASOB | SICKLEPOD | CASSIA OBTUSIFOLIA, L. |
| CHEAL | LAMBSQUARTERS, COMMON | CHENOPODIUM ALBUM, L. |
| IPOSS | MORNINGGLORY SPP. | IPOMOEA SPP. |
| SEBEX | SESBANIA, HEMP | SESBANIA EXALTATA, (RAF.) CORY |
| SINAR | MUSTARD, WILD | BRASSICA KABER, (DC) L.C.WHEELR |
| GLXMAW | SOYBEAN, WILLIAMS | GLYCINE MAX (L) MERR.CV.WILLIAMS |
| ORYSAT | RICE, TEBONNET | ORYZA SATIVA, L. TEBONNET |
| ZEAMX | CORN, FIELD | ZEA MAYS L. (SAMMEL-BEZEICHNUNG) |

| COMPOUNDS EVALUATED AS HERBICIDAL AGENTS | |
|---|---|
| Compound Number | |
| 1 | Diethyl {4-[(o-aminophenyl)thio]butyl}-phosphonate |
| 2 | {4-[(o-Aminophenyl)thio]butyl}phosphonic acid |
| 3 | Diethyl {4-[(o-aminophenyl)sulfonyl]butyl}-phosphonate |
| 4 | Dilithium {4-[(o-aminophenyl)thio]butyl}-phosphonate |

COMPOUNDS EVALUATED AS HERBICIDAL AGENTS

| Compound Number | |
|---|---|
| 5 | {4-[(o-Aminophenyl)thio]butyl}phosphonic acid, compound with cyclohexylamine (1:2) |
| 6 | Diethyl {4-[(o-aminophenyl)thio]-2-butenyl}phosphonate |
| 7 | {4-[(o-Hydroxyphenyl)thio]butyl}phosphonic acid |
| 8 | {4-[(o-Hydroxyphenyl)thio]butyl}phosphonic acid, compound with N,N,N',N'-tetramethylethylenediamine (1:1) |
| 9 | {4-[(o-Hydroxyphenyl)thio]butyl}phosphonic acid, compound with cyclohexylamine (1:2) |
| 10 | {4-[(o-Hydroxyphenyl)thio]butyl}phosphonic acid, compound with diisopropylamine (1:2) |
| 11 | {4-[(o-Hydroxyphenyl)thio]butyl}phosphonic acid, monoethyl ester |
| 12 | {4-[(o-Hydroxyphenyl)thio]-2-butenyl}phosphonic acid |
| 13 | Diethyl {4-[(o-hydroxyphenyl)thio]-2-butenyl}phosphonate |
| 14 | Dipivalate ester of bis(hydroxymethyl) {4-[(o-Hydroxyphenyl)thio]butyl}phosphonate |
| 15 | Diethyl {4-[(5-bromo-2-hydroxyphenyl)thio]-butyl}phosphonate |
| 16 | {4-[(2-Hydroxyphenyl)thio]butyl}phosphonic acid, aryl-benzoate ester |
| 17 | {4-[(o-Hydroxyphenyl)sulfinyl]butyl}phosphonic acid |
| 18 | {4-[(o-hydroxyphenyl)sulfonyl]butyl}phosphonic acid |
| 19 | {4-[(o-Hydroxyphenyl)sulfinyl]butyl}phosphonic acid, compound with cyclohexylamine (1:2) |
| 20 | {4-[(o-Hydroxyphenyl)thio]butyl}phosphonic acid, aryl-butyrate ester |
| 21 | {4-[(o-Hydroxyphenyl)thio]-1-butenyl}phosphonic acid |
| 22 | {4-[(o-Hydroxyphenyl)thio]-1-butenyl}phosphonic acid, compound with isopropylamine (1:2) |
| 23 | {4-[(5-Fluoro-2-hydroxyphenyl)thio]butyl}-phosphonic acid |
| 24 | Diethyl {4-[(5-fluoro-2-hydroxyphenyl)thio]butyl}phosphonate |
| 25 | {4-[(5-Fluoro-2-hydroxyphenyl)thio]butyl}phosphonic acid, compound with isopropylamine (1:2) |
| 26 | {4-[(o-Hydroxyphenyl)thio]butyl}phosphonic acid, diethyl ester, aryl-butyrate ester |
| 27 | {4-[(2-Amino-5-chlorophenyl)thio]butyl}-phosphonic acid |
| 28 | Diethyl {4-[(2-amino-5-chlorophenyl)thio]butyl}phosphonate |
| 29 | {4-[(5-Bromo-2-hydroxyphenyl)thio]butyl}-phosphonic acid |
| 30 | {4-[(2-Hydroxyphenyl)thio]butyl}phosphonic acid, diethyl ester, aryl-benzoate ester |
| 31 | {4-[o-Aminophenyl)thio]butyl}phosphonic acid, compound with N,N,N',N'-tetramethylethylenediamine (1:1) |
| 32 | Diethyl {4-[(o-hydroxyphenyl)thio]butyl}-phosphonate |
| 33 | {4-[(o-Aminophenyl)thio]-2-butenyl}phosphonic acid |
| 34 | {4-[2-Amino-5-bromophenyl)thio]butyl}phosphonic acid |
| 35 | {4-[(o-Aminophenyl)thio]butyl}phosphonic acid, monoethyl ester |

TABLE I

Herbicidal Evaluation of Test Compounds

| Compound Number | Rate (kg/ha) | AMASS | CASOB | CHEAL | IPOSS | SEBEX | SINAR | GLXMAW | ORYSAT | ZEAMX |
|---|---|---|---|---|---|---|---|---|---|---|
| 1 | 4.0 | 4.5 | — | 5.5 | 0.0 | — | 0.0 | 0.0 | — | 0.0 |
|   | 1.0 | 4.5 | — | 4.0 | 0.0 | — | 0.0 | 0.0 | — | 0.0 |
| 2 | 4.0 | — | — | 4.0 | 0.0 | 1.0 | 3.0 | 2.0 | — | 0.0 |
|   | 1.0 | — | — | 2.0 | 0.0 | 0.0 | 2.0 | 1.0 | — | 0.0 |
| 3 | 2.0 | 0.0 | — | 0.0 | 2.0 | — | — | 0.0 | — | 0.0 |
| 4 | 4.0 | 5.0 | — | 7.0 | 4.0 | — | — | 5.0 | — | 1.0 |
|   | 1.0 | 2.0 | — | 2.0 | 4.0 | — | — | 0.0 | — | 0.0 |
| 5 | 4.0 | 6.0 | — | 6.0 | 3.0 | — | — | 2.0 | — | 0.0 |
|   | 1.0 | 5.0 | — | 5.0 | 2.0 | — | — | 0.0 | — | 0.0 |
| 6 | 4.0 | 3.0 | — | 0.0 | 0.0 | — | — | 1.0 | — | 2.0 |
| 7 | 8.0 | — | — | 0.0 | 3.0 | 8.0 | 6.0 | 8.0 | 0.0 | 0.0 |
|   | 4.0 | — | 3.7 | 3.1 | 2.0 | 5.1 | 3.4 | 6.5 | 0.1 | 0.1 |
|   | 2.0 | — | 2.4 | 2.6 | 1.4 | 4.4 | 3.2 | 5.6 | 0.0 | 0.2 |
| 8 | 8.0 | — | — | 0.0 | 1.0 | 7.0 | 3.0 | 6.0 | 0.0 | 0.0 |
|   | 4.0 | — | — | 0.0 | 0.0 | 7.0 | 3.0 | 6.0 | 0.0 | 0.0 |
| 9 | 8.0 | — | — | 0.0 | 0.0 | 7.0 | 3.0 | 7.0 | 0.0 | 0.0 |
|   | 4.0 | — | 1.0 | 0.8 | 0.2 | 3.8 | 2.2 | 4.6 | 0.0 | 0.0 |
| 10 | 8.0 | — | — | 0.0 | 1.0 | 7.0 | 3.0 | 8.0 | 0.0 | 0.0 |
|    | 4.0 | — | — | 0.0 | 1.0 | 7.0 | 1.0 | 7.0 | 0.0 | 0.0 |
| 11 | 4.0 | — | 3.0 | 3.0 | 1.0 | 6.0 | 1.0 | 7.0 | 0.0 | 0.0 |
|    | 2.0 | — | 4.0 | 1.0 | 0.0 | 5.0 | 0.0 | 7.0 | 0.0 | 0.0 |
| 12 | 4.0 | — | — | 3.0 | 1.0 | 2.0 | 3.0 | 6.0 | 0.0 | 0.0 |
|    | 2.0 | — | 1.0 | — | 1.0 | 2.0 | 3.0 | 6.0 | 0.0 | 0.0 |
| 13 | 4.0 | — | 0.0 | 2.0 | 0.0 | 0.0 | 0.0 | 0.0 | 0.0 | 0.0 |
|    | 2.0 | — | 0.0 | 1.0 | 0.0 | 0.0 | 0.0 | 0.0 | 0.0 | 0.0 |
| 14 | 4.0 | — | 6.0 | 3.0 | 2.0 | 7.0 | 3.0 | 7.0 | 0.0 | 1.0 |

TABLE I-continued

Herbicidal Evaluation of Test Compounds

| Compound Number | Rate (kg/ha) | AMASS | CASOB | CHEAL | IPOSS | SEBEX | SINAR | GLXMAW | ORYSAT | ZEAMX |
|---|---|---|---|---|---|---|---|---|---|---|
|  | 2.0 | — | 3.0 | 3.0 | 1.0 | 4.0 | 3.0 | 7.0 | 0.0 | 0.0 |
| 15 | 4.0 | — | 0.0 | 4.0 | 0.0 | 0.0 | 0.0 | 0.0 | 0.0 | 0.0 |
|  | 2.0 | — | 0.0 | 0.0 | 0.0 | 0.0 | 0.0 | 0.0 | 0.0 | 0.0 |
| 16 | 4.0 | — | 3.0 | 2.0 | 0.0 | 5.0 | 2.0 | 7.0 | 0.0 | 0.0 |
| 17 | 2.0 | — | 4.0 | 4.0 | 2.0 | 7.0 | 3.0 | 7.0 | 0.0 | 0.0 |
| 18 | 4.0 | — | 0.0 | 1.0 | 0.0 | 0.0 | 0.0 | 0.0 | 0.0 | 0.0 |
| 19 | 4.0 | — | — | 2.0 | 4.0 | 5.0 | 6.0 | 6.0 | 0.0 | 0.0 |
|  | 2.0 | — | 4.0 | 0.0 | 4.0 | 6.0 | 5.0 | 7.0 | 0.0 | 1.0 |
| 20 | 2.0 | — | 4.0 | 1.0 | 4.0 | 7.0 | 3.0 | 8.0 | 0.0 | 0.0 |
| 21 | 4.0 | — | 6.0 | 6.0 | 3.0 | 7.0 | 7.0 | 8.0 | 1.0 | 2.0 |
| 22 | 4.0 | 7.0 | 4.0 | 4.0 | 4.0 | 7.0 | 7.0 | 7.0 | 0.0 | 2.0 |
|  | 2.0 | 6.0 | 4.0 | 4.0 | 3.0 | 6.0 | 6.0 | 7.0 | 0.0 | 0.0 |
| 23 | 4.0 | 2.0 | 1.0 | 2.0 | 1.0 | 5.0 | 2.0 | 7.0 | 0.0 | 0.0 |
| 24 | 4.0 | 2.0 | 0.0 | 3.0 | 1.0 | 0.0 | 0.0 | 0.0 | 0.0 | 0.0 |
| 25 | 4.0 | 2.0 | 1.0 | 3.0 | 0.0 | 1.0 | 2.0 | 7.0 | 0.0 | 0.0 |
| 26 | 1.0 | — | 0.0 | 0.0 | 0.0 | 0.0 | 0.0 | 0.0 | 0.0 | 0.0 |
| 27 | 4.0 | — | — | 0.0 | 0.0 | 0.0 | 0.0 | 0.0 | 0.0 | 0.0 |
| 28 | 4.0 | — | — | 0.0 | 0.0 | 0.0 | 0.0 | 0.0 | 0.0 | 0.0 |
| 29 | 4.0 | — | 0.0 | 0.0 | 0.0 | 0.0 | 0.0 | 0.0 | 0.0 | 0.0 |
| 30 | 4.0 | — | 0.0 | 0.0 | 0.0 | 0.0 | 0.0 | 0.0 | 0.0 | 0.0 |
| 31 | 4.0 | — | — | 0.0 | 0.0 | 0.0 | 0.0 | 0.0 | 0.0 | 0.0 |
| 32 | 4.0 | — | — | 0.0 | 0.0 | 0.0 | 0.0 | 0.0 | 0.0 | 0.0 |
| 33 | 4.0 | 0.0 | — | 0.0 | 0.0 | — | — | 0.0 | 0.0 | 0.0 |
| 34 | 4.0 | 0.0 | — | 0.0 | 0.0 | — | — | 0.0 | 0.0 | 0.0 |
| 35 | 4.0 | 0.0 | — | 0.0 | 0.0 | — | — | 0.0 | — | 0.0 |

What is claimed is:

1. A compound having the structural formula

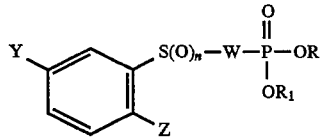

wherein

Y is hydrogen or halogen;
Z is $NH_2$ or $OR_2$;
$R_2$ is hydrogen, $C_1$–$C_4$alkylcarbonyl or benzoyl;
n is an integer of 0, 1 or 2;
W is —$(CH_2)_4$—, —$CH_2CH=CHCH_2$— or —$CH_2CH_2CH=CH$—; and
R and $R_1$ are each independently hydrogen, $C_1$–$C_4$alkyl, $C_1$–$C_4$alkylcarbonyloxymethylene or an alkali metal, ammonium or organic ammonium cation, provided that where W is —$(CH_2)_4$— and Z is $NH_2$ then at least one of R and $R_1$ is other than $C_1$–$C_4$ alkyl.

2. The compound according to claim 1 wherein
Y is hydrogen, F or Br;
n is an integer of 0 or 1;
W is —$(CH_2)_4$— or —$CH_2CH_2CH=CH$—; and
R and $R_1$ are each independently hydrogen, $C_1$–$C_4$alkyl, $C_1$–$C_4$alkylcarbonyloxymethylene or an alkali metal or organic ammonium cation.

3. A compound selected from the group consisting of
{4-[(o-hydroxyphenyl)thio]-1-butenyl}phosphonic acid;
{4-[(o-hydroxyphenyl)thio]-1-butenyl}phosphonic acid;
dilithium {4-[(o-aminophenyl)thio]butyl}phosphonate;
dipivalate ester of bis(hydroxymethyl) {4-[(o-hydroxyphenyl)thio]butyl}phosphonate;
{4-[(o-hydroxyphenyl)thio]butyl}phosphonic acid, compound with N N N',N'-tetramethylethylenediamine;
{4-[(o-hydroxyphenyl)sulfinyl]butyl}phosphonic acid;
{4-[(o-hydroxyphenyl)thio]butyl}phosphonic acid, arylbutyrate ester; and mixtures thereof.

4. The compound according to claim 3 {4-[(o-hydroxyphenyl)thio]-1-butenyl}phosphonic acid.

5. The compound according to claim 3 dilithium {4-[(o-aminophenyl)thio]butyl}phosphonate.

6. The compound according to claim 3 dipivalate ester of bis(hydroxymethyl) {4-[(o-hydroxyphenyl)thio]butyl}phosphonate.

7. The compound according to claim 2 {4-[(o-hydroxyphenyl)thio]butyl}phosphonic acid, compound with N,N,N',N'-tetramethylethylenediamine.

8. The compound according to claim 3 {4-[(o-hydroxyphenyl)sulfinyl]butyl}phosphonic acid.

9. The compound according to claim 3 {4-[(o-hydroxyphenyl)thio]butyl}phosphonic acid, arylbutyrate ester.

10. A mixture comprising a compound selected from the group consisting of
{4-[(o-aminophenyl)thio]butyl}phosphonic acid;
{4-[(o-hydroxyphenyl)sulfinyl]butyl}phosphonic acid; and
{4-[(o-hydroxyphenyl)thio]-1-butenyl}phosphonic acid, in combination with an aliphatic or cycloaliphatic amine.

11. The mixture of claim 10 wherein the aliphatic amine is cyclohexylamine.

12. The mixture of claim 10 wherein the cycloaliphatic amine is isopropylamine.

13. The mixture of claim 11 wherein cyclohexlamine is in an amount greater than the compound.

14. The mixture of claim 12 wherein isopropylamine is in an amount greater than the compound.

15. The mixture according to claim 13 comprising
{4-[(o-aminophenyl)thio]butyl}phosphonic acid and cyclohexylamine in a ratio of 1:2.

16. The mixture according to claim 13 comprising {4-[(o-hydroxyphenyl)sulfinyl]butyl}phosphonic acid and cyclohexylamine in a ratio of 1:2.

17. The mixture according to claim 14 comprising {4-[(o-hydroxyphenyl)thio]-1-butenyl}phosphonic acid and isopropylamine in a ratio of 1:2.

18. A herbicidal composition which comprises an inert solid or liquid carrier and a herbicidally effective amount of a compound having the structural formula

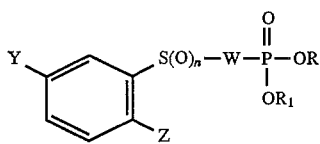

wherein

Y is hydrogen or halogen;

Z is $NH_2$ or $OR_2$;

$R_2$ is hydrogen, $C_1$-$C_4$alkylcarbonyl or benzoyl;

n is an integer of 0, 1 or 2;

W is —$(CH_2)_4$—, —$CH_2CH$=$CHCH_2$— or —$CH_2CH_2CH$=$CH$—; and

R and $R_1$ are each independently hydrogen, $C_1$-$C_4$alkyl, C1-C4alkylcarbonyloxymethylene or an alkali metal, ammonium or organic ammonium cation, provided that where W is —$(CH_2)_4$— and Z is $NH_2$ then at least one of R and $R_1$ is other than $C_1$-$C_4$alkyl.

19. The composition according to claim 18 wherein

Y is hydrogen, F or Br;

n is an integer of 0 or 1;

W is —$(CH_2)_4$— or —$CH_2CH_2CH$=$CH$—; and

R and $R_1$ are each independently hydrogen, $C_1$-$C_4$alkyl, $C_1$-$C_4$alkylcarbonyloxymethylene or an alkali metal or organic ammonium cation.

20. A method for controlling undesirable plant species which comprises applying to the foliage and stems of said plants a herbicidally effective amount of a compound having the structural formula

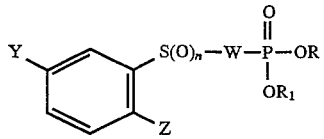

wherein

Y is hydrogen or halogen;

Z is $NH_2$ or $OR_2$;

$R_2$ is hydrogen, $C_1$-$C_4$alkylcarbonyl or benzoyl;

n is an integer of 0, 1 or 2;

W is —$(CH_2)_4$—, —$CH_2CH$=$CHCH_2$— or —$CH_2CH_2CH$=$CH$—; and

R and $R_1$ are each independently hydrogen, $C_1$-$C_4$alkyl, $C_1$-$C_4$alkylcarbonyloxymethylene or an alkali metal, ammonium or organic ammonium cation.

21. The method according to claim 20 wherein

Y is hydrogen, F or Br;

n is an integer of 0 or 1;

W is —$(CH_2)_4$— or —$CH_2CH_2CH$=$CH$—; and

R and $R_1$ are each independently hydrogen, $C_1$-$C_4$alkyl, $C_1$-$C_4$alkylcarbonyloxymethylene or an alkali metal or organic ammonium cation.

22. The method according to claim 21 wherein the compound is selected from the group consisting of {4-[(o-hydroxyphenyl)thio]-1-butenyl}phosphonic acid;

diethyl {4-[(o-aminophenyl)thio]butyl}phosphonate;

dilithium {4-[(o-aminophenyl)thio]butyl}phosphonate;

{4-[(o-aminophenyl)thio]butyl}phosphonic acid, compound with cyclohexylamine (1:2);

dipivalate ester of bis(hydroxymethyl) {4-[(o-hydroxyphenyl)thio]butyl}phosphonate;

{4-[(o-hydroxyphenyl)sulfinyl]butyl}phosphonic acid, compound with cyclohexylamine (1:2);

{4-[(o-hydroxyphenyl)thio]butyl}phosphonic acid, compound with N,N,N',N'-tetramethylethylenediamine;

{4-[(o-hydroxyphenyl)sulfinyl]butyl}phosphonic acid;

{4-[(o-hydroxyphenyl)thio]butyl}phosphonic acid, arylbutyrate ester; and

{4-[(o-hydroxyphenyl)thio]-1-butenyl}phosphonic acid, compound with isopropylamine (1:2).

23. The method according to claim 20 which comprises applying said compound to the foliage and stems of said plants at a rate of about 0.5 kg/ha to 10 kg/ha.

24. The method according to claim 20 wherein the undesirable plant is lambsquarters or wild mustard.

* * * * *